United States Patent [19]
Jaeger et al.

[11] Patent Number: 5,900,638
[45] Date of Patent: May 4, 1999

[54] RADIATION PROTECTION ARRANGEMENT FOR AN X-RAY DIAGNOSTICS INSTALLATION

[75] Inventors: Wolfgang Jaeger, Neunkirchen; Stefan Leidenberger, Effeltrich; Rainer Kraemer, Fuerth, all of Germany

[73] Assignee: Siemens Aktiengesellschaft, Munich, Germany

[21] Appl. No.: 08/827,313

[22] Filed: Mar. 26, 1997

[30] Foreign Application Priority Data

Mar. 26, 1996 [DE] Germany .............................. 196 11 982
Mar. 27, 1996 [DE] Germany .............................. 196 12 215
May 13, 1996 [DE] Germany .............................. 196 19 297

[51] Int. Cl.$^6$ ........................................................ G21F 3/02
[52] U.S. Cl. ...................................... 250/519.1; 250/515.1
[58] Field of Search .............................. 250/515.1, 516.1, 250/519.1

[56] References Cited

U.S. PATENT DOCUMENTS 4,062,518  12/1977  Stivender et al. .................... 250/519.1
4,581,538   4/1986  Lenhart ................................ 250/515.1

FOREIGN PATENT DOCUMENTS 1075813   10/1954  France .
1466848    2/1969  Germany .
2313201    9/1974  Germany .
30 124 63  6/1989  Germany .
196 19 297 2/1997  Germany .

*Primary Examiner*—Bruce Anderson
*Attorney, Agent, or Firm*—Hill & Simpson

[57] ABSTRACT

In a radiation protection arrangement for an x-ray diagnostics installation, at least one x-ray impenetrable strap is pivotably seated at a carrier, this being movable along a guide rail via the carrier. A brake arrangement for the carrier is provided which at least impedes movement of the carrier along the guide rail when the component of the installation on which the radiation protection arrangement is carried is adjusted in position. At least two x-ray impenetrable straps can be provided, each being pivotably seated at a carrier, whereby a formed part is provided in the region of the carrier which effects a diversion of each strap during pivoting. Each strap can be capable of being folded over and fixed in the folded-over condition, so that an opening to the examination region is produced.

24 Claims, 7 Drawing Sheets

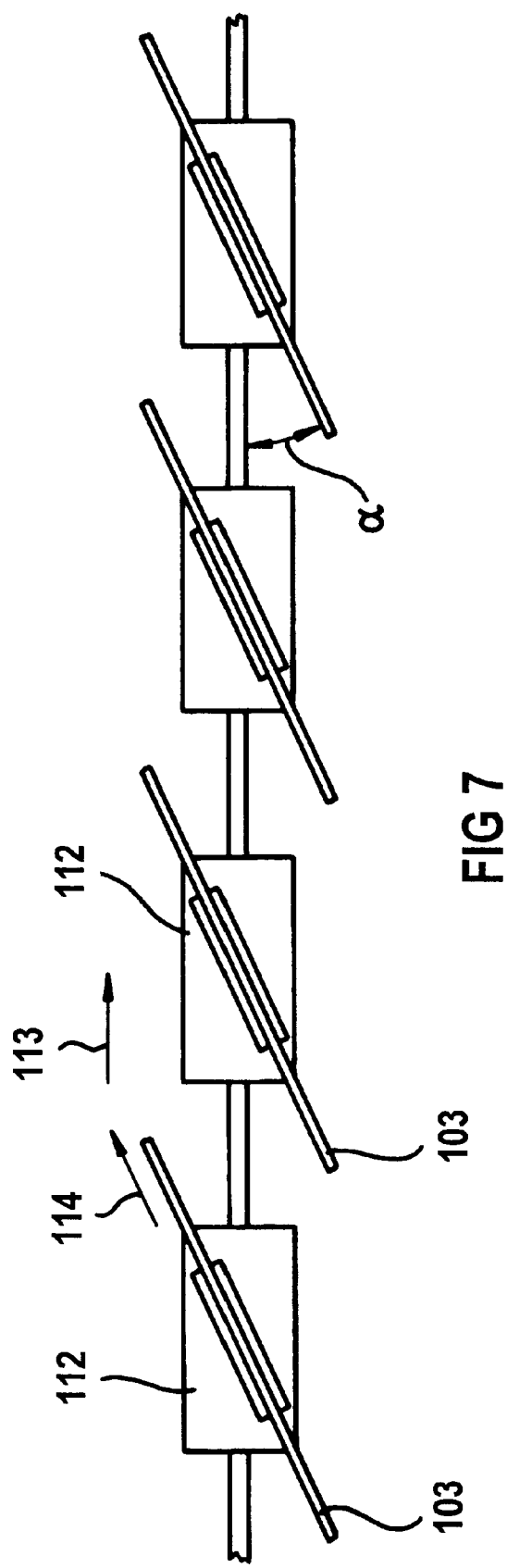

RADIATION PROTECTION ARRANGEMENT FOR AN X-RAY DIAGNOSTICS INSTALLATION

BACKGROUND OF THE INVENTION

1. Field of the Invention

The present invention is directed to an arrangement for protecting attending personnel from x-rays emitted by an x-ray source in an x-ray diagnostics installation.

2. Description of the Prior Art

German OS 30 12 463 discloses a radiation protection arrangement for an x-ray aiming device comprised of lead-rubber straps pivotedly suspended at a carrier. The carrier has two carrying elements connected to one another in articulated fashion that are adjustable via button-like guide elements at guide rails secured to the x-ray aiming device. The supporting elements can describe an angle relative to one another. The lead-rubber straps are secured to the two carrying elements of the carrier overlapping one another in the fashion of roofing tiles. The carrying element is guided at a lateral guide rail of the x-ray aiming device and is angled and has comb-like projections at which the lead-rubber straps are seated in articulated fashion. Another lower carrying element is fabricated of an elastically resilient flat material to which the lead-rubber straps are riveted flat at a number of locations. The lead-rubber straps are pivotable around a rotational axis at the comb-like projections of the carrying element. A number of lead-rubber straps are arranged at each carrying element.

German OS 196 19 297 discloses a radiation protection arrangement for an x-ray diagnostics installation that has a carrier at which a lead-rubber flap is pivotably seated. The carrier is adjustable at a guide rail. A carrier is provided for each lead-rubber flap and the carriers are connected chain-like to one another via a connecting element. The lead-rubber straps are seated at the respective carrier pivotable around a transverse axis, so that a good radiation protection is assured both given a horizontal as well as given a vertical alignment of the x-ray aiming device together with an allocated support platform for an examination subject.

When the x-ray aiming device is pivoted from the horizontal into the vertical alignment, then the lead-rubber straps are moved in the guide rail via their carrier as a result of the force of gravity and thus proceed into a limit position.

SUMMARY OF THE INVENTION

It is an object of the present invention to provide a radiation protection arrangement for an x-ray diagnostics installation of the type initially described which does not allow the lead-rubber straps to be unintentionally moved in the guide rail.

This above object is achieved in accordance with the principles of the present invention in a radiation protection arrangement for an x-ray diagnostics installation having a guide rail surrounding a region in which x-rays are emitted, with a number of lead-rubber straps each having a carrier movable seated in the guide rail, and a brake arrangement for each carrier which at least impedes, and preferably prevents, movement of the carriers along the guide rail when the component to which the guide rail is attached is adjusted in position.

An advantage of the invention is that an movement of the carrier along the rail is intentionally initiated by the operator and does not occur independently, such as by the force of gravity.

It is advantageous for the braking arrangement to be a as friction brake or a mechanism which engages at the carrier, preferably at an end of the carrier. The position of the radiation protection arrangement can thus be fixed to achieve an optimum radiation protection.

A further object of the present invention is to provide a radiation protection arrangement for an x-ray diagnostics installation of the type initially described wherein the lead-rubber straps do not seize or become impeded when the x-ray aiming device is pivoted.

The above object is achieved in accordance with the principles of the present invention in a radiation protection arrangement for an x-ray diagnostics installation having at least two lead-rubber straps which are pivotably seated at a carrier, each strap having a formed part in the region of the carrier which effects a diversion of the lead-rubber strap when the strap is caused to pivot out of a perpendicular position.

An advantage of providing a formed part at the carrier is that the lead-rubber straps are diverted at this formed part when pivoted, without the lead-rubber straps seizing or becoming impeded.

It is particularly advantageous when, for this purpose, the formed part is fashioned as a bead surrounded by a swiveling axis of the lead-rubber strap fashioned as a ring. To this end, the formed part can be placed into or placed on the lead-rubber strap.

It is advantageous for the same purpose when the lead-rubber straps are joined to one another in a first direction and are aligned in a second direction, with the first and second directions describing a non-zero angle relative to one another. As a result, seizing and impeding of the lead-rubber straps when pivoting the x-ray aiming device is also prevented.

Lead-rubber straps pivotally suspended at a carrier are provided in the radiation protection arrangement disclosed by German OS 30 12 463. These lead-rubber straps serve as radiation protection but impede access to the examination subject. It is therefore also an additional object of the invention to provide a radiation protection arrangement of the type initially described wherein this access is facilitated.

This object is achieved in accordance with the principles of the present invention in a radiation protection arrangement for an x-ray diagnostic installation wherein at least one lead-rubber strap is movably arranged in a guide rail so as to prevent radiation from being emitted beyond a region surrounding an x-ray source, and wherein the radiation protection strap can be folded over, and fixed in a folded-over position, so as to allow access to the protected region.

An advantage of the invention is that the at least one lead-rubber strap can be folded over and fixed in the folded-over position. Access to the examination subject is thereby produced and the access is maintained.

DESCRIPTION OF THE DRAWINGS

FIG. 7 shows a modification of the radiation protection of the invention in elevation.

DESCRIPTION OF THE PREFERRED EMBODIMENTS

Figure 1:
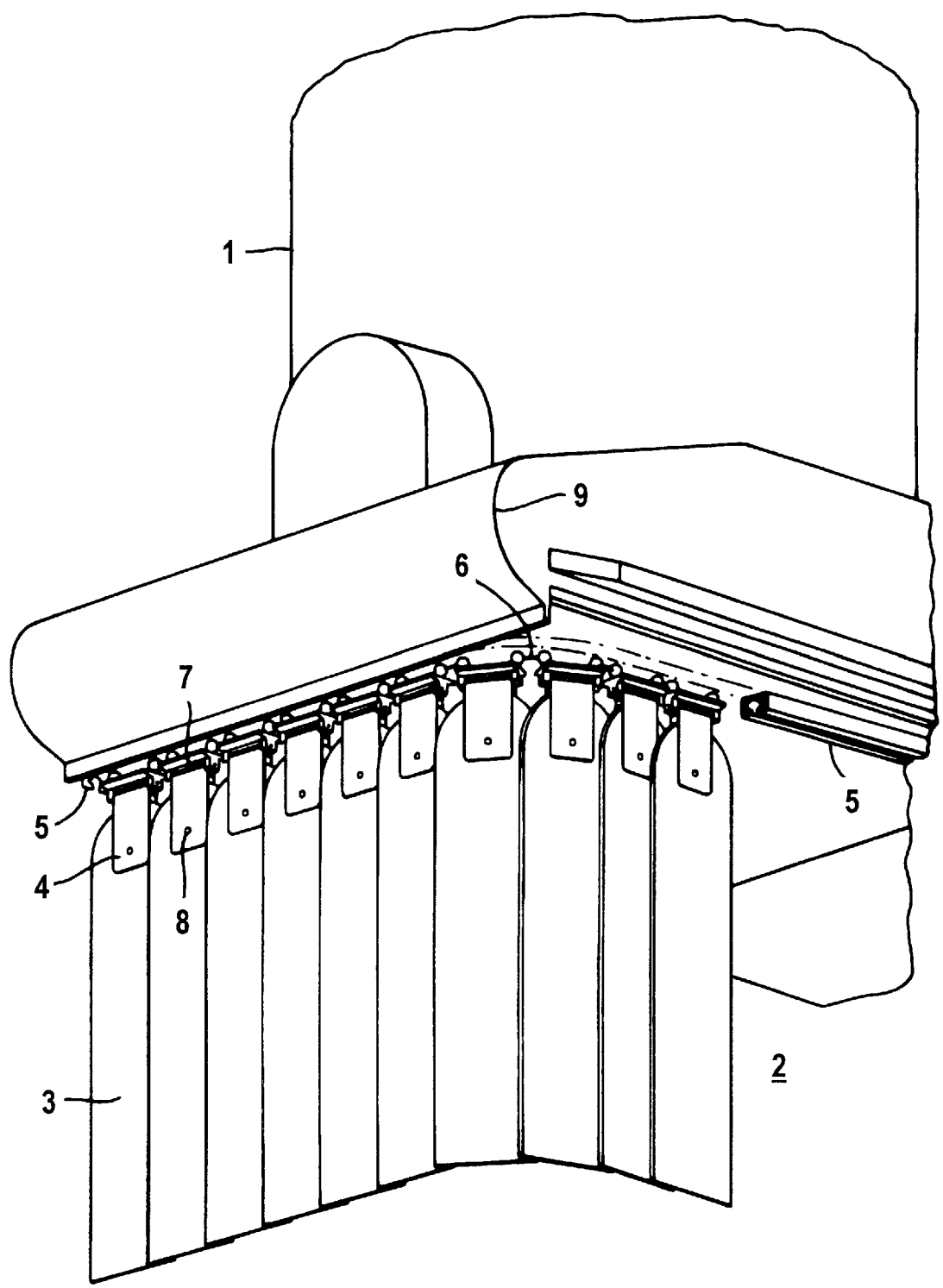
FIG. 1 is a schematic illustration of an x-ray diagnostics installation with a radiation protection arrangement constructed in accordance with the principles of the present invention.

FIG. 1 shows an x-ray diagnostics installation 1 that, for example, is an x-ray aiming device. The x-ray aiming device is usually arranged over a support platform or bed for an examination subject, and has a radiation protection arrangement 2 disposed at least one side facing toward the patient support. This radiation protection arrangement 2 has at least one lead-rubber strap 3, preferably a number of lead-rubber straps 3, joined to one another but movably seated in a guide rail 5 via a carrier 4. Each lead-rubber strap 3 preferably is seated in its own carrier 4. When a number of carriers 4 are provided, it is advantageous to join them chain-like to one another via a connecting element 6. For example, a cable, a revolute joint or a flexible rod can be employed as each connecting element 6. The lead-rubber straps 3 are seated at the respective carrier 4 pivotable around a transverse axis 7 and, expediently, also pivotable around a rotational axis 8 oriented substantially perpendicularly relative to the axis 7. When, for example, the x-ray aiming device 1 is adjusted a vertical alignment, then the lead-rubber straps 3 are also moved toward the right, i.e., downward by the force of gravity, in the guide rail 5 via their carriers 4.

Figure 2:
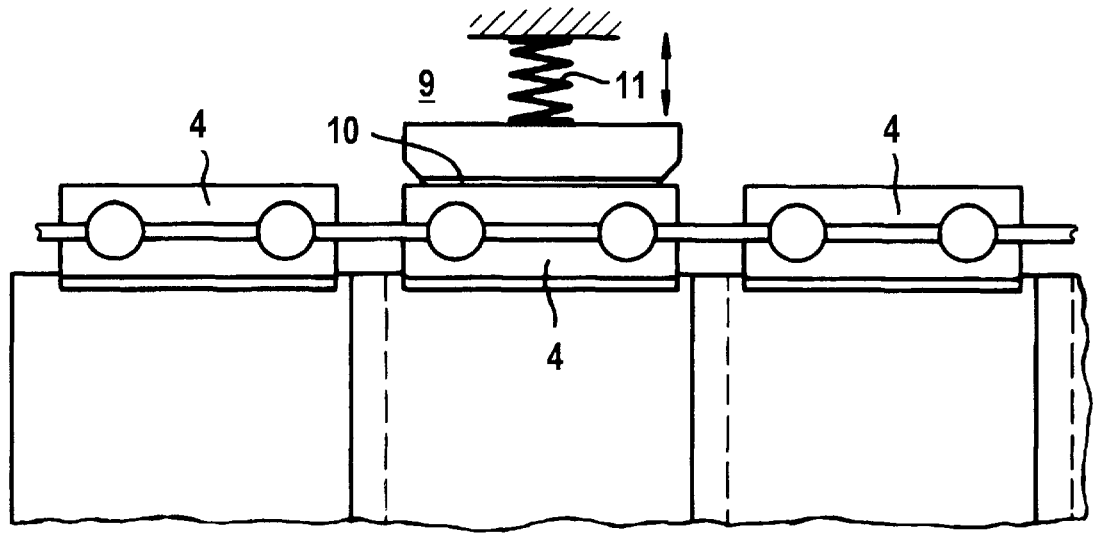
FIG. 2 shows a radiation protection arrangement of the invention in a side view, with a friction brake.

In order to prevent an independent or unintentional movement of the lead-rubber straps 3 or at least to make this more difficult during such an adjustment of the x-ray aiming device, a brake arrangement 9 for the carrier 4 is inventively provided. In the embodiment shown in FIG. 2 the brake arrangement 9 is a friction brake whose brake lining 10 engages at the carrier 4 preferably loaded by a resilient element 11, for example a coil spring.

Figure 3:
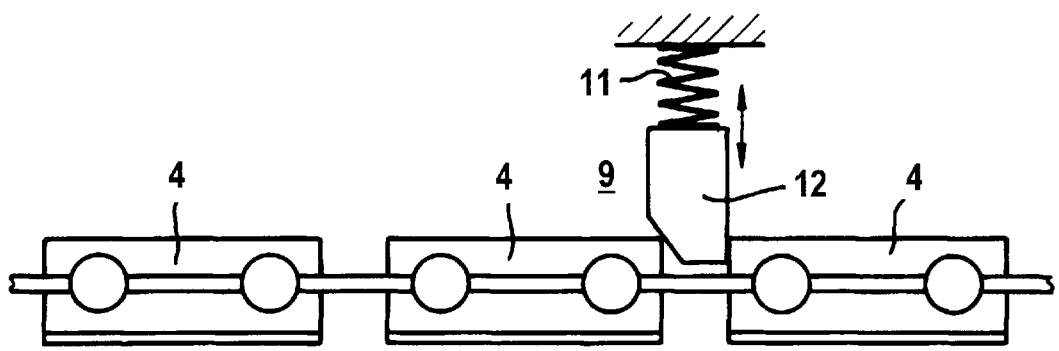
FIG. 3 shows a modification of the radiation protection arrangement of FIG. 1 with a brake element engaging at the carrier.

According to a modification shown in FIG. 3, the brake arrangement 9 is implemented such that it engages the carrier 4. Structurally, a peg 12 can be provided for this purpose that engages into a recess at the carrier 4. Conversely, of course, a recess at the brake arrangement 9 can engage a peg of the carrier 4. If a number of carriers 4 are attached to one another chain-like, then the peg 12 can also engage between two carriers 4. To this end, the peg 12 can likewise be adjusted in the direction toward the carrier 4 by a resilient element 11.

Figure 4:
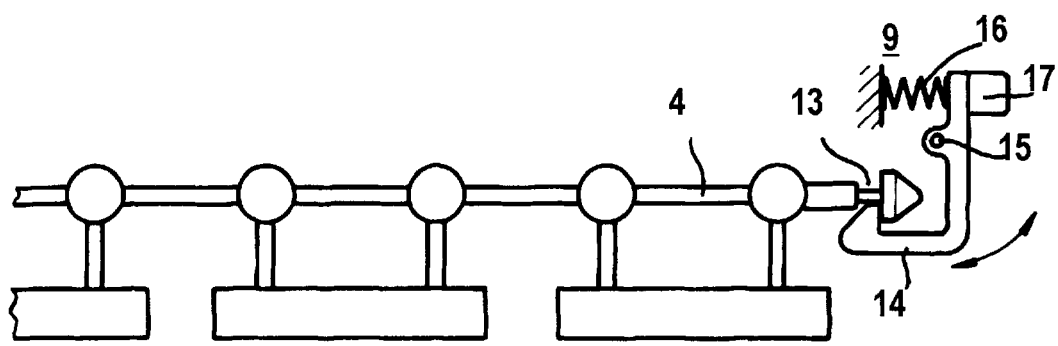
FIG. 4 shows another modification of the radiation protection arrangement of FIG. 1 with a brake element engaging an end of at the carrier.

In another modification of the invention shown in FIG. 4, a brake arrangement 9 is provided at the carrier 4 at the end thereof, this brake arrangement 9, for example, being fashioned as a catch 14 engaging into a channel 13. The catch 14 is pivotable around an axis 15 and, loaded by a resilient element 16, engages in the channel 13. The locking can be released in all modifications of the invention by an unlocking mechanism 17.

The unlocking mechanism 17 is preferably implemented as a lever arrangement so as to enable an easy cancellation of the interlock or brake.

Figure 6:
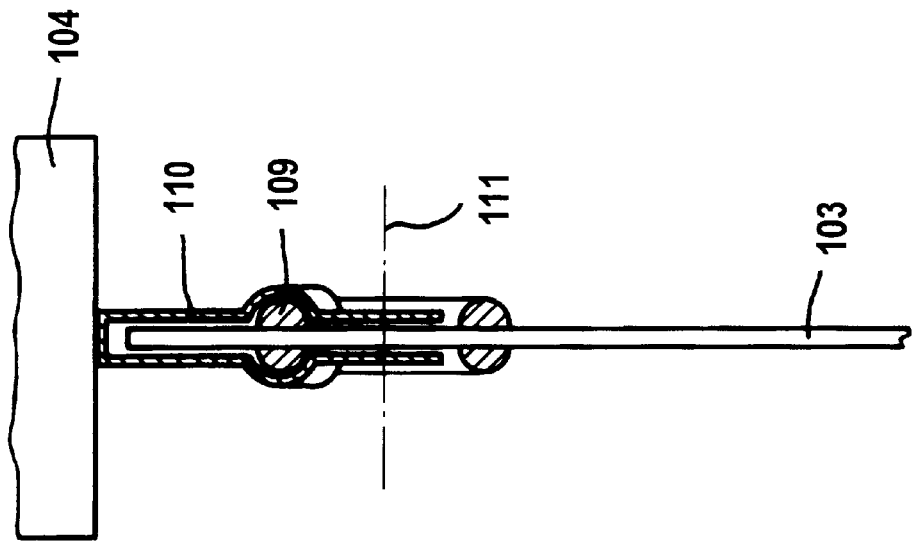
FIG. 6 shows the radiation protection of FIG. 5 in a side view.
Figure 5:
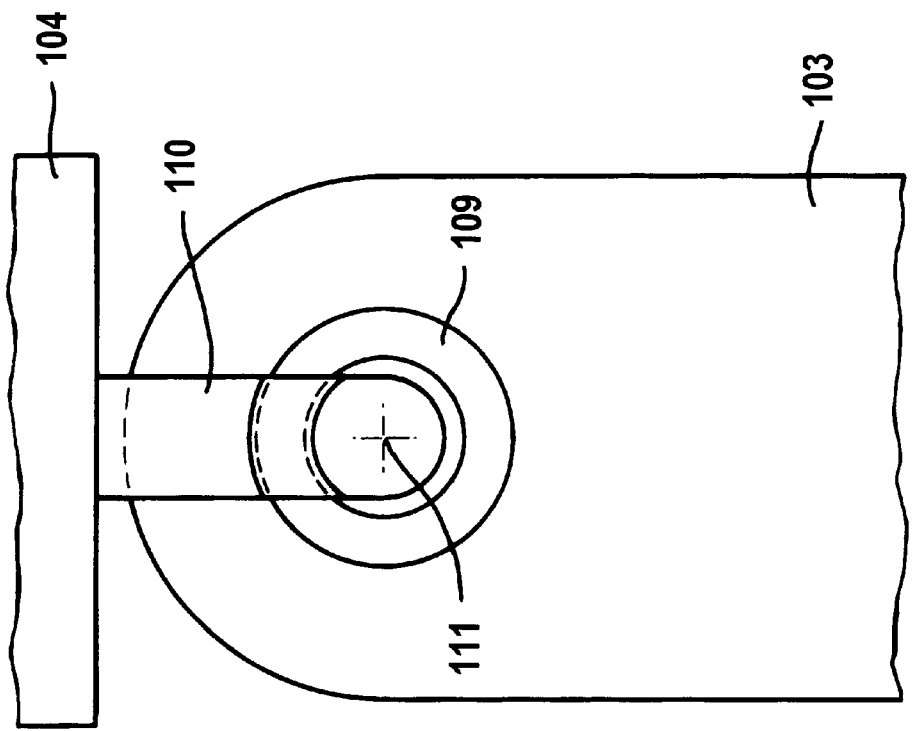
FIG. 5 shows a radiation protection of the invention in a plan view.

FIGS. 5 and 6 schematically show a carrier 104 with a lead-rubber strap 103, with a formed part 109 inventively provided at the carrier 104 which effects a diversion of a lead-rubber strap 103 when the radiation protection means is pivoted. As can be seen in FIG. 6, the formed part 109 is fashioned as a bead at a retainer part 110. The preferably annular bead of the formed part 109 surrounds a swiveling axis 111 and can be placed in the lead-rubber straps 103 or placed on them.

In the modification of the radiation protection arrangement of the invention shown in FIG. 7, at least two lead-rubber straps 103 are pivotably seated in respective carriers 112. The carriers 112 allow the straps 103 to be are seated such that they are joined to one another in a first direction 113 and are aligned in a second direction 114. The first and second directions 113 and 114 describe an angle a relative to one another. If a number of carriers 112 for respective lead-rubber straps 103 are adjoined to one another in a chain-like manner, then lead-rubber straps 103 neighboring one another should at least partially overlap order to assure a reliable radiation protection.

Figure 9:
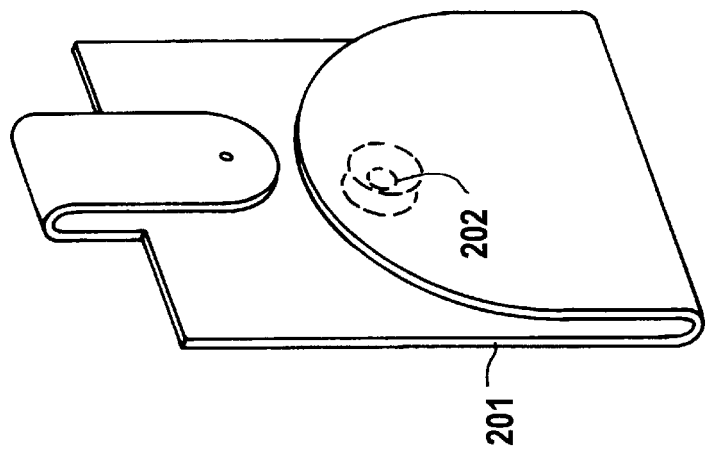
FIG. 9 shows the a radiation protection strap of FIG. 8 in the folded condition.
Figure 8:
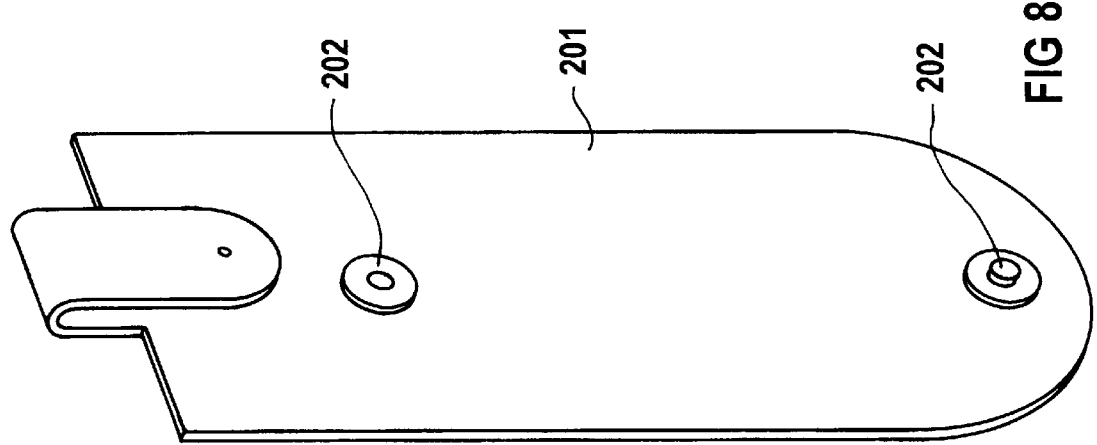
FIG. 8 shows a first exemplary embodiment of a radiation protection strap in the non-folded condition.
Figure 11:
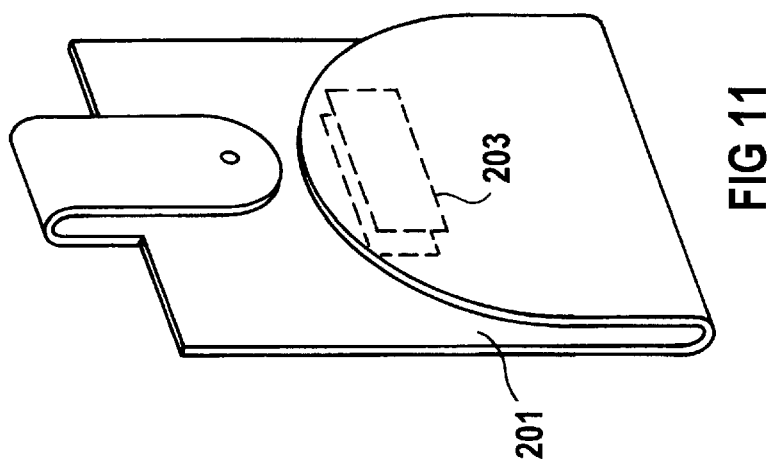
FIG. 11 shows the radiation protection strap of FIG. 10 in the folded condition.
Figure 10:
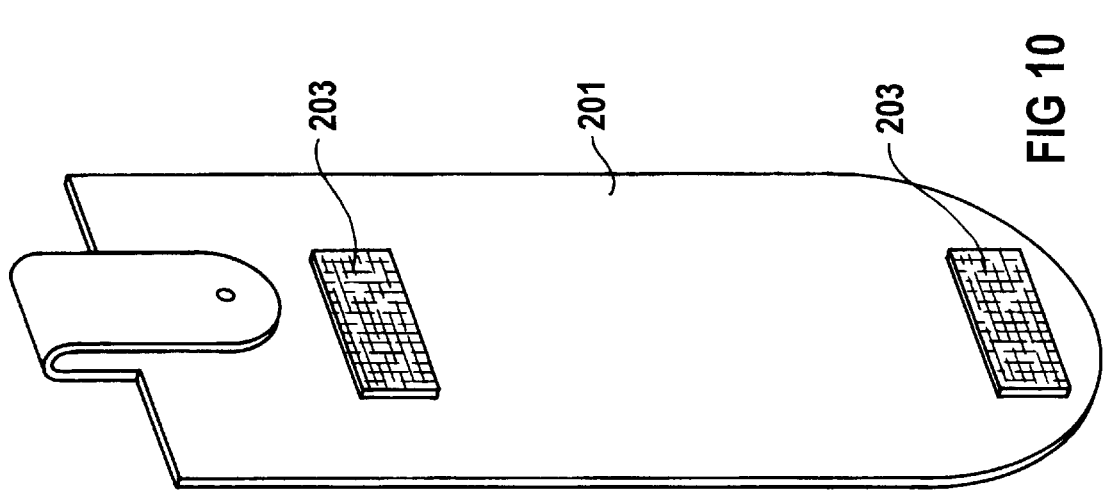
FIG. 10 shows a second exemplary embodiment of a radiation protection strap in the non-folded condition.
Figure 13:
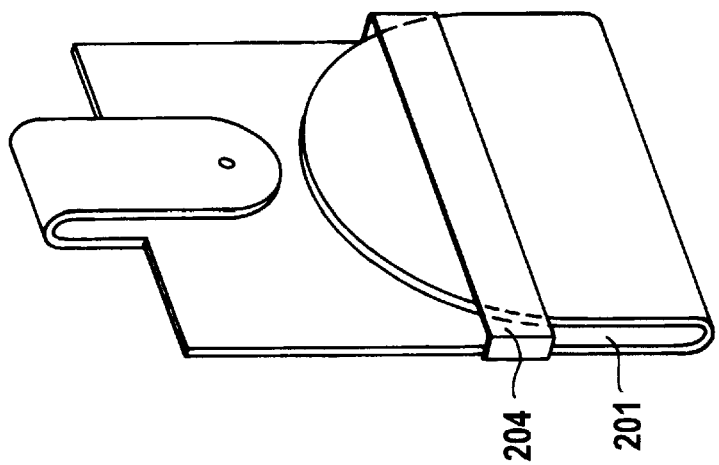
FIG. 13 shows the radiation protection strap of FIG. 12 in the folded condition.
Figure 12:
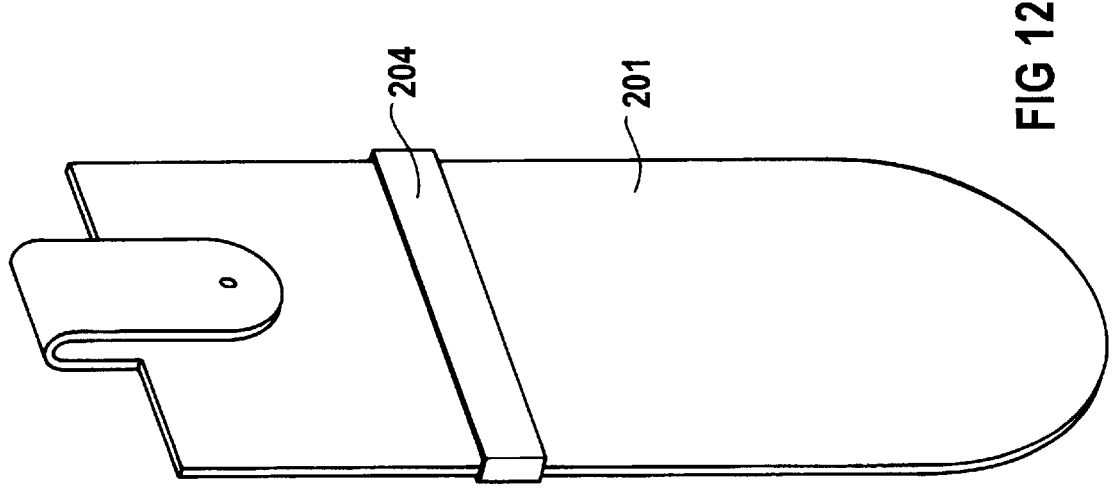
FIG. 12 shows another exemplary embodiment of a radiation protection strap in the non-folded condition.

In FIGS. 8 and 9, a lead-rubber strap 201 is shown which can be adjustable along a guide rail, particularly in an x-ray aiming device. According to the invention, the lead-rubber straps 201 can be folded (FIGS. 9, 11, 13) from an extended, i.e., suspended condition (FIGS. 8, 10, 12) and can be fixed in the folded-over condition. A snap fastener 202 according to FIGS. 8 and 9 a hook and loop closure 203 according to FIGS. 10 and 11, a clip 204 according to FIGS. 12 and 13 or a magnet means (not shown) are suitable for the fixing. The fixing can be provided at the front side or back side and can be glued, welded or sewn to the lead-rubber strap 201. The opening that is produced by folding the lead-rubber strap 201 up can be set dependent on the position of the fixing means. A number of retaining positions can be provided at the lead-rubber strap 1, so that differently sized openings can be achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray diagnostics installation having an x-ray source which emits x-rays and including at least one component adjustable in position, the improvement of a radiation protection arrangement for preventing x-rays from emerging from a protected area, said improvement comprising:

a guide rail attached to said component;
   a plurality of x-ray-impenetrable straps each having a carrier and each carrier being movably mounted in said guide rail; and
   brake means for mechanically interacting with said carriers for at least impeding movement of said carriers in said guide rail when said component is adjusted in position.

2. The improvement of claim 1 wherein all of said carriers are connected together in a chain.

3. The improvement of claim 2 wherein said brake means comprises means for engaging at one of said carriers.

4. The improvement of claim 2 wherein said brake means comprises means for engaging between two adjacent ones of said carriers.

5. The improvement of claim 2 wherein said brake mans comprises means for engaging an end of the carriers connected in a chain.

6. The improvement of claim 1 wherein said brake means comprises a friction brake.

7. The improvement of claim 6 wherein said friction brake comprises a brake lining and a resilient element which forces said brake lining into engagement with at least one carrier.

8. The improvement of claim 1 wherein said x-ray source and said component comprise an x-ray aiming device.

9. In an x-ray diagnostic installation having an x-ray source which emits x-rays and including at least one component adjustable in position, the improvement of a radiation protection arrangement for preventing x-rays from emerging from a protected area, said improvement comprising:

a guide rail attached to said component;

at least two x-ray-impenetrable straps each having a carrier and each carrier being pivotably mounted in said guide rail, and each carrier having a formed part for diverting the strap attached to that carrier when that strap is pivoted; and brake means for mechanically interacting with said carriers for at least impeding movement of said carriers in said guide rail when said component is adjusted in position.

10. The improvement of claim 9 wherein said formed part comprises a bead.

11. The improvement of claim 10 wherein said bead is disposed at a retainer portion of the carrier.

12. The improvement of claim 10 wherein each annular strap has a swiveling axis, and wherein said bead comprises an annular bead surrounding said swiveling axis.

13. The improvement of claim 9 wherein said formed part is integrally embedded in said strap.

14. The improvement of claim 9 wherein said formed part is attached to said strap.

15. In an x-ray diagnostic installation having an x-ray source which emits x-rays and including at least one component adjustable in position, the improvement of a radiation protection arrangement for preventing x-rays from emerging from a protected area, said improvement comprising:

a guide rail attached to said component;

at least two x-ray-impenetrable straps each having a carrier and each carrier being movably mounted in said guide rail;

brake means for mechanically interacting with said carriers for at least impeding movement of said carriers in said guide rail when said component is adjusted in position; and means for mounting the respective carriers of said at least two x-ray-impenetrable straps relative to said x-ray source for preventing x-rays from emerging from a protected area, said means for mounting comprising means for joining said at least two x-ray-impenetrable straps to each other in a first direction and for aligning said at least two x-ray-impenetrable straps in a second direction, said first and second directions having a non-zero angle relative to each other.

16. The improvement of claim 15 wherein said means for mounting comprises means for aligning said at least two x-ray-impenetrable straps substantially parallel to each other in said second direction.

17. The improvement of claim 15 wherein the respective carriers of said at least two x-ray-impenetrable straps are connected to each other in a chain.

18. The improvement of claim 15 wherein said means for mounting includes a guide rail surrounding said x-ray source.

19. In an x-ray diagnostic installation having an x-ray source which emits x-rays and including at least one component adjustable in position, the improvement of a radiation protection arrangement for preventing x-rays from emerging from a protected area, said improvement comprising:

a guide rail attached to said component;

a plurality of x-ray-impenetrable straps each having a carrier and each carrier being movably mounted in said guide rail;

brake means for mechanically interacting with said carriers for at least impeding movement of said carriers in said guide rail when said component is adjusted in position; and at least one of said x-ray-impenetrable straps being comprised of foldable material, and means for fixing said at least one x-ray impenetrable strap in a folded-over position for permitting access to said protected area.

20. The improvement of claim 19 wherein said means for fixing comprises a snap fastener.

21. The improvement of claim 19 wherein said means for fixing comprises a hook-and-loop fastener.

22. The improvement of claim 19 wherein said means for fixing comprises a clip.

23. The improvement of claim 19 wherein said means for fixing comprises a magnet connection.

24. The improvement of claim 19 wherein said means for fixing comprises means for fixing said at least one x-ray-impenetrable strap in a plurality of selectable folded-over positions.

* * * * *